US012557975B2

(12) United States Patent
Lo et al.

(10) Patent No.: US 12,557,975 B2
(45) Date of Patent: Feb. 24, 2026

(54) FLEXIBLE ENDOSCOPE WITH DETACHABLE HEAD AND HANDLE

(71) Applicant: Precision Robotics (Hong Kong) Limited, Shatin (HK)

(72) Inventors: Ping Lai Benny Lo, Shatin (HK); Yang Hu, Shatin (HK); Siu Lun Alan Kwok, Shatin (HK); Sotiris Tsouris, Shatin (HK); Sai Yan Ng, Shatin (HK)

(73) Assignee: Precision Robotics (Hong Kong) Limited, Shatin (HK)

( * ) Notice: Subject to any disclaimer, the term of this patent is extended or adjusted under 35 U.S.C. 154(b) by 522 days.

(21) Appl. No.: 18/003,929

(22) PCT Filed: Jun. 29, 2021

(86) PCT No.: PCT/CN2021/102888
§ 371 (c)(1),
(2) Date: Dec. 30, 2022

(87) PCT Pub. No.: WO2022/001994
PCT Pub. Date: Jan. 6, 2022

(65) Prior Publication Data
US 2023/0263376 A1 Aug. 24, 2023

(30) Foreign Application Priority Data
Jun. 30, 2020 (HK) ........................... 22020010223.8

(51) Int. Cl.
*A61B 1/005* (2006.01)
*A61B 1/00* (2006.01)
(Continued)

(52) U.S. Cl.
CPC ........ *A61B 1/0057* (2013.01); *A61B 1/00105* (2013.01); *A61B 1/0052* (2013.01);
(Continued)

(58) Field of Classification Search
CPC . A61B 1/0057; A61B 1/00105; A61B 1/0052; A61B 1/05; A61B 34/30; A61B 34/71
See application file for complete search history.

(56) References Cited

U.S. PATENT DOCUMENTS 11,284,956 B2     3/2022  Zemlok et al.
2008/0087871 A1*   4/2008  Schena ................... F16H 19/06
                                                 254/226
(Continued)

FOREIGN PATENT DOCUMENTS

CN        102171006 A    8/2011
CN        103648362 A    3/2014
(Continued)

OTHER PUBLICATIONS

International Search Report from PCT International Application No. PCT/CN2021/102888, dated Sep. 28, 2021.
(Continued)

*Primary Examiner* — Anh Tuan T Nguyen
*Assistant Examiner* — Rynae E Boler
(74) *Attorney, Agent, or Firm* — Budzyn IP Law, LLC

(57) ABSTRACT

A flexible endoscope system is provided for use in surgical operation which includes a head part and a control handle detachably connected using first and second docking keys. The head part comprises a shaft, a flexible tip located at a distal end of the shaft, an image sensor module, and drive tendons extending in the shaft for controlling the movement of the flexible tip in multiple degrees of freedom. The control handle includes multiple motors for tensioning or relaxing the drive tendons via a capstan assembly. Control element is provided on the control handle to allow a user to trigger a complex movement of the flexible tip to form an S shape so that a bird-eye view of the surgical site can be obtained by the endoscope system. The detachable connec-
(Continued)

tion eliminates the need to sterilize the control handle in which the main electronic components are located.

17 Claims, 7 Drawing Sheets

(51) Int. Cl.

| | |
|---|---|
| *A61B 1/05* | (2006.01) |
| *A61B 1/313* | (2006.01) |
| *A61B 34/00* | (2016.01) |
| *A61B 34/30* | (2016.01) |

(52) U.S. Cl.
CPC ............... *A61B 1/05* (2013.01); *A61B 1/313* (2013.01); *A61B 2034/301* (2016.02); *A61B 2034/715* (2016.02)

(56) References Cited

U.S. PATENT DOCUMENTS

| | | | |
|---|---|---|---|
| 2013/0012959 A1 | 1/2013 | Jinno | |
| 2014/0135685 A1* | 5/2014 | Kabe | A61F 2/246 |
| | | | 604/95.04 |
| 2014/0257333 A1* | 9/2014 | Blumenkranz | A61B 34/71 |
| | | | 606/130 |
| 2015/0011830 A1* | 1/2015 | Hunter | A61B 1/0016 |
| | | | 600/118 |
| 2015/0230697 A1* | 8/2015 | Phee et al. | |
| 2016/0199138 A1* | 7/2016 | Cooper | A61B 34/70 |
| | | | 606/130 |
| 2018/0168760 A1 | 6/2018 | Koch, Jr. et al. | |
| 2019/0175287 A1 | 6/2019 | Hill et al. | |
| 2019/0247128 A1* | 8/2019 | Inouye | A61B 34/20 |
| 2020/0237460 A1* | 7/2020 | Rockrohr | A61B 34/32 |
| 2021/0113068 A1* | 4/2021 | Shin | A61B 1/0055 |
| 2022/0015847 A1* | 1/2022 | Kadokura | A61B 34/37 |

FOREIGN PATENT DOCUMENTS

| | | | |
|---|---|---|---|
| CN | 104138295 A | 11/2014 | |
| CN | 104755041 A | 7/2015 | |
| CN | 104883991 A | 9/2015 | |
| CN | 105025829 A | 11/2015 | |
| CN | 106236003 A | 12/2016 | |
| CN | 109219414 A | 1/2019 | |
| JP | 2010253162 A | 11/2010 | |
| JP | 2019521736 A | 8/2019 | |
| WO | 2006059721 A1 | 6/2006 | |
| WO | 2019222058 A1 | 11/2019 | |
| WO | 2021127426 A1 | 6/2021 | |

OTHER PUBLICATIONS

Office Action from Hong Kong Patent Application No. 22020010223. 8, dated Oct. 14, 2022.

* cited by examiner

FLEXIBLE ENDOSCOPE WITH DETACHABLE HEAD AND HANDLE

CROSS-REFERENCE TO RELATED APPLICATIONS

This Application is a National Stage Application under 35 U.S.C. § 371 of PCT Application No. PCT/CN2021/102888, filed Jun. 29, 2021, which claims priority to Hong Kong Patent Application No. 22020010223.8, filed Jun. 30, 2020, the entire contents of which are incorporated by reference herein.

BACKGROUND OF THE INVENTION

1. Field of the Invention

The present invention relates to endoscope system, in particular, a flexible endoscope for use in both robot-assisted surgery and in traditional manual surgery.

2. Description of the Related Art

Single-port access surgery (SPAS) is a recently developed technique in surgery. It is a minimally invasive surgical procedure in which the surgeon operates almost exclusively through a single entry point. Unlike a traditional multi-port approach, SPAS leaves only a single small scar.

Surgical robotic arms are often used to assist the doctors in the single-port access surgery. Generally, a surgical robot instrument comprises a base, a positioning arm and a surgical robotic arm. The surgical robotic arm can be hold at a desired location by the positioning arm. An endoscope can be mounted to an end of the surgical robotic arm. The surgical robotic arm enters the patient's body at a single port to implement surgical operations.

Conventional endoscopes are multi-use and require sterilization to avoid cross-contamination. Standard sterilization methods may require the device to be put in a high pressure, high temperature, or poisonous gas environment. As motors and other electronic components are integrated into the endoscope, they may be damaged in the sterilization process. Further, sterilization also involves packaging and logistic cost.

The present invention seeks to overcome the aforementioned drawbacks in the conventional endoscopes.

SUMMARY OF THE INVENTION

According to an aspect of the present disclosure, an endoscope system is provided. The endoscope system comprises a head part and a control handle. A docking interface is formed between the control handle and the head part to allow a detachable connection. The key electronic components (e.g. motor, controller) are positioned in the handle which does not require sterilization. The head part, designed to be inserted into human body, only contains minimal electronic components with a lower cost. By separating the head part from the handle part, the head part can be disposable and only requires one sterilization process after manufacturing.

In one embodiment, the endoscope system comprising a heat part and a control handle. The head part comprising a shaft, at least one drive tendon extending in the shaft, a flexible tip located at a distal end of the shaft, movement of the flexible tip being controlled by the drive tendon, a connecting interface located at a proximal end of the shaft, the connecting interface including at least one capstan assembly around which the drive tendon is wound; and an image sensor module arranged on the flexible tip. The control handle is detachably connected to the connecting interface. The capstan assembly includes a capstan shaft having a first docking key, and the control handle includes a second docking key, when the control handle is coupled to the connecting interface, the second docking key mates with the first docking key such that movement of the second docking key can be transmitted to the capstan assembly via the first docking key to adjust the tension in the drive tendon.

In one embodiment, one of the first and second docking keys has a projecting portion, and the other of the first and second docking keys has a recessed portion complementary in shape. At least one of the first and second docking keys is provided with a guiding portion to facilitate the engagement between the first and second docking keys.

In one embodiment, the connecting interface includes a tendon guide near a proximal end of the shaft. At least a portion of an inner wall of the tendon guide is provided with a guide groove for receiving and guiding a segment of the drive tendon between the proximal end of the shaft and the capstan assembly. The connecting interface further includes a base located between the proximal end of the shaft and the tendon guide. A hole is formed on the base for receiving one end of the capstan shaft. A bearing is arranged in the hole for rotatably supporting the capstan shaft.

In one embodiment, a pair of drive tendon is wound on one capstan assembly. The capstan assembly includes two positioning rings along the capstan shaft. Each positioning rings has an axially extending portion on which one drive tendon in the pair is wound and a stopper for holding an end of the drive tendon. A fastening hole is provided on the positioning ring for receiving a fastener used to lock the positioning ring on the capstan shaft.

In one embodiment, the connecting interface further includes an end cover on which openings are formed for receiving an electrical connector and an optical fiber connector. The control handle includes a circuit board connected to the electric connector by means of a pogo pin connector.

In one embodiment, the control handle includes at least one motor, and the second docking key is coupled to an output end of the motor.

In one embodiment, the connecting interface includes three capstan assemblies. A pair of drive tendons is wound around each capstan assembly to control the movement of the flexible tip in one degree of freedom. The control handle includes three motors for independently actuating the three capstan assemblies.

In one embodiment, one or more control elements are provided on the control handle. At least one control element is preset or programmed to control one or more motors to trigger a movement of the flexible tip and/or the image sensor module. The control element is preset or programmed to cause the flexible tip to exhibit an S shape so that a bird-eye view of a surgical site can be obtained by the image sensor module.

In one embodiment, a locking means is provided on the control handle. The locking means includes a latch and an operating member movable by a user to engage the latch with or disengage the latch from a catch slot formed on the connecting interface. The locking means further includes a rod along which the operating member is slidable and an elastic element for biasing the operating member to a locking position. The latch is coupled to the operating member via a linkage mechanism which converts a sliding movement of the operating member into a rotational motion <table>
<tr><td>3</td><td>4</td></tr>
</table> of the latch. The linkage mechanism includes an elongated slot on the latch and a bar on the operating member. The elongated slot is oriented at an angle relative to a longitudinal direction such that movement of the bar in the elongated slot causes the latch to rotate.

In one embodiment, the control handle includes a bracket for supporting the at least one motor. A circuit board is arranged between the bracket and a housing of the control handle. The bracket has two curved surfaces for supporting the motor. The two curved surfaces are separated by a tubular structure which defines a slot or a tube for receiving a functional element, such as an optical fiber cable.

In one embodiment, the head part is disposable and the control handle is durable.

In one embodiment, the flexible tip includes at least one flexible joint, each flexible joint comprises two support sections and an articulating section connected therebetween. The articulating section includes a plurality of segments each provided with at least one contact assisting part. The contact assisting parts of adjacent segments are in contact with each other when the flexible joint bends. The segments can be connected with each other to form a helical articulating section. Alternatively, the segments can be separate rings or discs.

In one embodiment, a pair of contact assisting parts is arranged at diametrically opposite positions on each segment. At least one tendon hole or slot through which a drive tendon passes is formed on each segment.

It is to be understood that both the foregoing general description and the following detailed description are exemplary and explanatory only and are not restrictive of the embodiments, as claimed.

BRIEF DESCRIPTION OF THE DRAWINGS

The accompanying drawings are included to provide a further understanding of the invention described herein and are incorporated in and constitute a part of this specification. The drawings illustrate exemplary embodiments. Certain features may be better understood by reference to the following detailed description when considered in connection with the accompanying drawings, in which like reference numerals designate like parts throughout the figures thereof, and wherein.

DETAILED DESCRIPTION OF THE EMBODIMENTS

Figure 1:
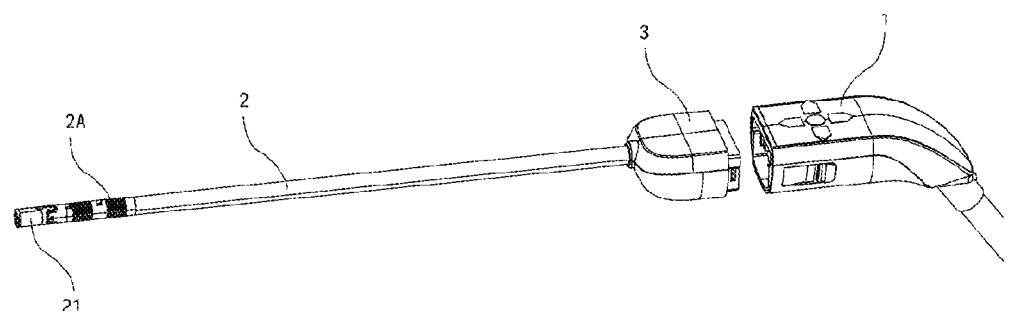
FIG. 1 shows an endoscope system according to one embodiment of the invention.

FIG. 1 shows an endoscope system having a shaft 2 in which one or more drive tendons 4 extend. The shaft 2 may be rigid or may include a bendable part and a non-bendable part of the surgical robotic arm. When performing a single-port surgery, the bendable part of the shaft 2 is inserted into the human body and advances in a body channel such as trachea, esophagus, intestine, vagina, etc.

A flexible tip 2A is located at the distal end of the shaft 2. The flexible tip 2A is movable with multiple degrees of freedom. Movement of the flexible tip 2A is controlled by the drive tendons 4. The drive tendons 4 can be provided in pairs. In use, when one drive tendon 4 is tensioned, the other drive tendon in the pair is relaxed such that the flexible tip 2A bends toward the direction of the tensioned drive tendon.

An image sensor module 21 is arranged on the flexible tip 2A. The image sensor module 21 provides a close view of the surgical site to the physician. Alternatively, the image sensor module can be replaced by other surgical instruments, such as a clamp or a laser scalpel, to perform a desired function in the operation.

Figure 2:
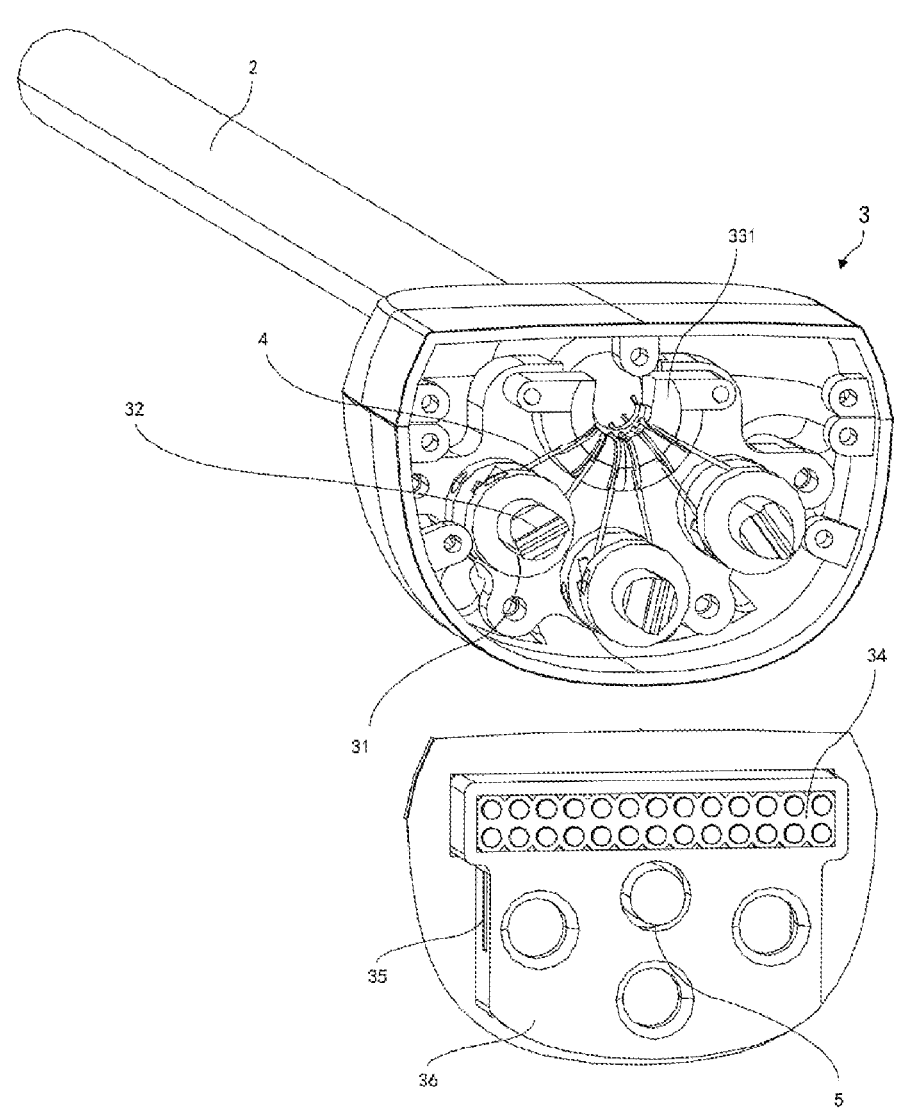
FIG. 2 shows a connecting interface of the endoscope system according to one embodiment of the invention.

A connecting interface 3 is provided at the proximal end of the shaft 2. As illustrated in FIG. 2, the connecting interface 3 includes one or more capstan assemblies 31 around which the drive tendons 4 are wound. The connecting interface 3 is designed to be detachably coupled to the control handle 1 so that the control handle 1 can be separated from the shaft 2 and the flexible tip 2A before and after the surgical operation.

The detachable connection between the control handle 1 and the connecting interface 3 reduces the risk of cross-contamination since the components on the connecting interface side (invasive part) can be designed for single use. The invasive part of the endoscope system may require sterilization. Nevertheless, since the main electronic components, including motor, controller and circuit board, are arranged on the control handle side (non-invasive part), sterilization of the invasive part does not damage the main electronic components.

Figure 3A:
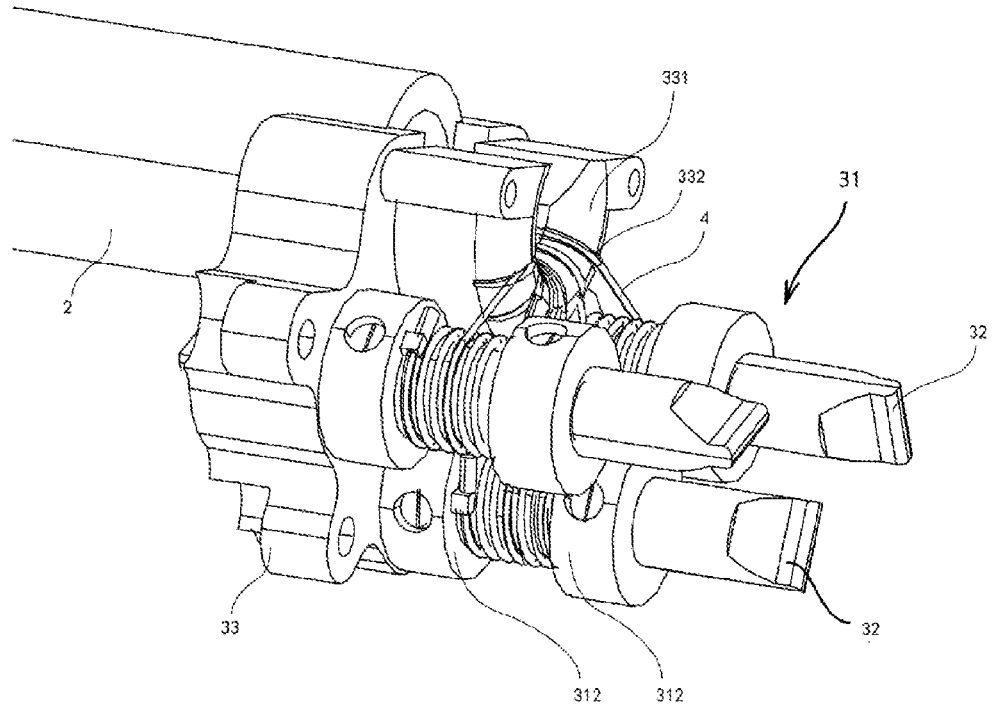
FIGS. 3A and 3B are enlarged views showing components in the connecting interface in FIG. 2.
Figure 3B:
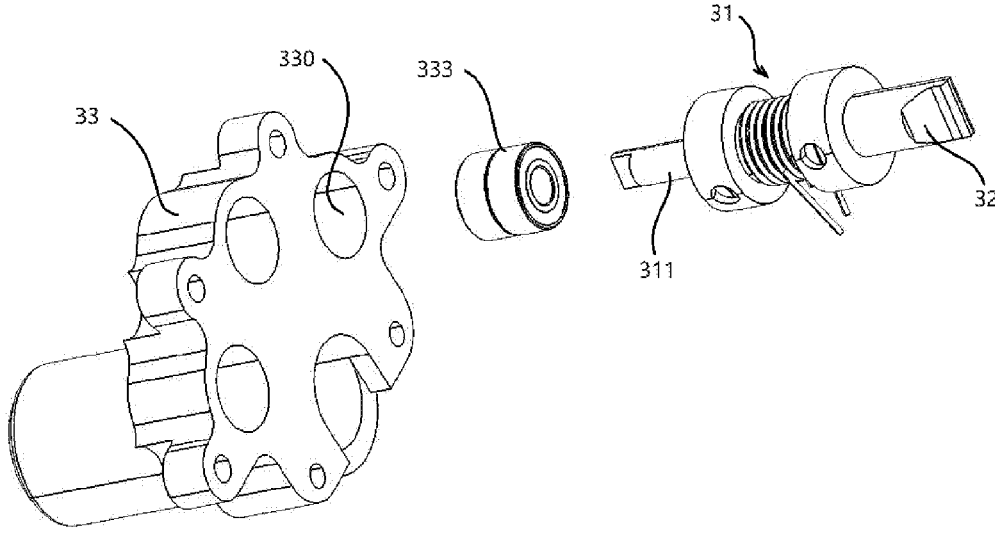

FIGS. 3A and 3B show the components in the connecting interface 3. A tendon guide 331 is located near a proximal end of the shaft. A guide groove 332 is formed on at least a portion of an inner wall of the tendon guide 331. The guide groove 33 receives a segment of the drive tendon 4 between the proximal end of the shaft 2 and the capstan assembly 31. A base 33 is located between the proximal end of the shaft 2 and the tendon guide 331. As seen in FIG. 3B, a hole 330 is formed on the base 33 for receiving one end of the capstan shaft 311. A bearing 333 is arranged in the hole 330 for rotatably supporting the capstan shaft 311.

Figure 4:
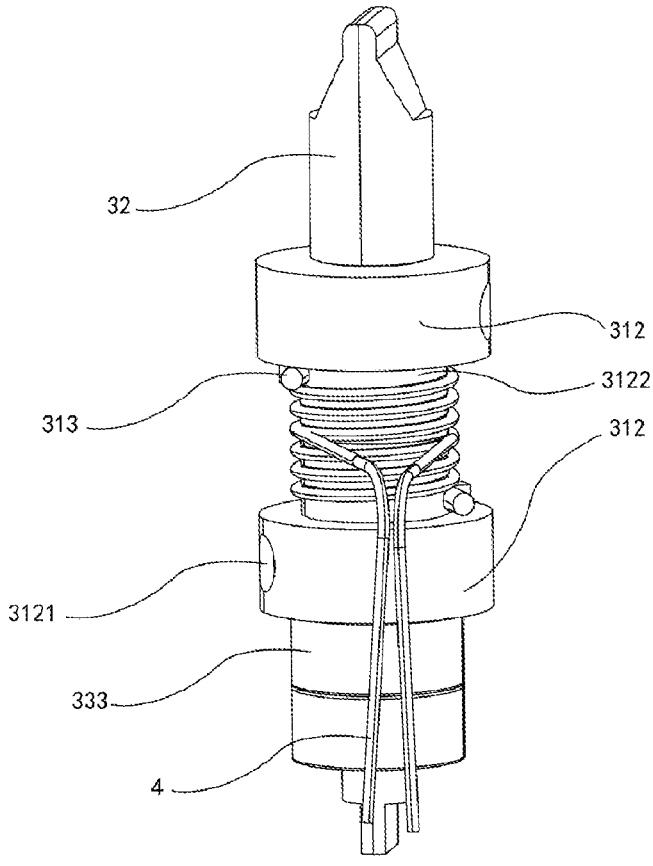
FIG. 4 shows the capstan assembly in the connecting interface.

Referring to FIG. 4, the capstan assembly 31 includes a capstan shaft 311 and two positioning rings 312 along the capstan shaft 311. A first docking key 32 is provided at one end of the capstan shaft 311. The first docking key 32 can be integrally formed with the capstan shaft 311 or can be a separate element mounted to the capstan shaft 311. The first docking key 32 is configured to engage a second docking key 13 provided on the control handle 1 when the connecting interface 3 is coupled to the control handle 1. Engagement between the first docking key 32 and the second docking key 13 allows the movement of the second docking key 13 to be transmitted to the capstan assembly 31 via the first docking key 32 to adjust the tension in the drive tendon 4.

Figure 5:
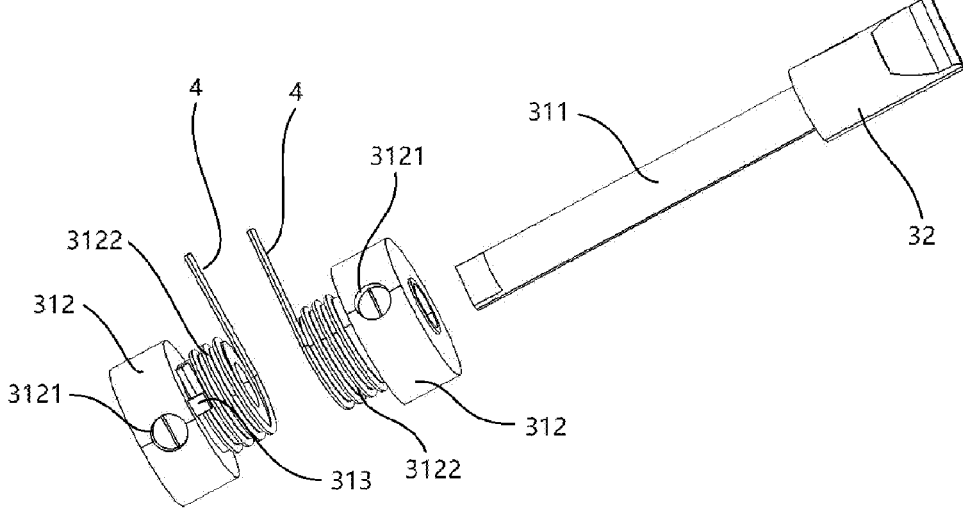
FIG. 5 is an exploded view of the capstan assembly.

In the embodiment shown in FIG. 5, a pair of drive tendon 4 is wound on one capstan assembly 31. The capstan assembly 31 includes two positioning rings 312 along the capstan shaft 311. Each positioning rings 312 has an axially extending portion 3122 on which one drive tendon 4 in the pair is wound. A fastening hole 3121 can be formed on the positioning ring 312 for receiving a fastener used to secure the positioning ring 312 on the capstan shaft 311. For example, the fastening hole 3121 can be threaded to receive a screw. The retaining ring 312, when secured to the capstan shaft 311 by the fastener, rotates with the capstan shaft 311. A tendon stopper 313 is formed on the positioning ring 312 to secure one end of the drive tendon 4. Rotation of the capstan assembly 31 in one direction tensions one drive tendon 4 and relaxes the other drive tendon 4 in the pair. Tensioning and relaxing of the drive tendons 4 control the movement of the flexible tip 2A on the shaft 2.

The position of the tendon stopper 313 relative to the capstan shaft 311 is changeable. A user can remove the fastener, rotate the positioning ring 312 to a desired position, and then use the fastener to lock the position of the positioning ring 312 on the capstan shaft 311. This allows a user to adjust the tension in the drive tendon 4.

Figure 6:
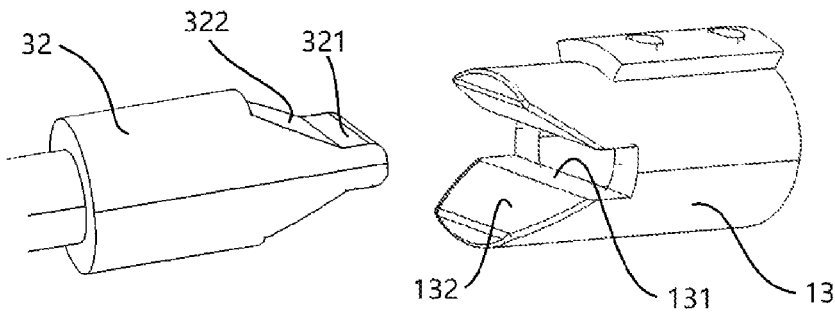
FIG. 6 shows a docking key design according to one embodiment of the invention.

One embodiment of the docking key design is illustrated in FIG. 6. The first docking key 32 comprises a projecting portion 321, such as a key. The second docking key 13 comprises a recessed portion 131 complementary in shape, such as a key slot. By simply inserting the projecting portion 321 into the recessed portion 131, a transmission path between the first docking key 32 and the second docking key 13 is established. Preferably, at least one of the first and second docking keys is provided with a guiding portion to facilitate the engagement. In FIG. 6, inclined surfaces 322, 132 are formed on both of the first docking key 32 and the second docking key 13 to guide the projecting portion 321 into the recessed portion 131. It is contemplated that the first docking key 32 can be shaped to have a recessed portion and the second docking key 13 has a projecting portion. Preferably, the first docking key 32 can be made of a plastic material to save manufacturing cost of the single use components, while the second docking key 13 can be made of metal to improve the durability of the control handle 1.

Optionally, referring back to FIG. 2, the connecting interface 3 includes an end cover 36 having openings which allow the first docking keys 32 to engage the second docking keys 13. The end cover 36 further has an elongated opening for receiving an electrical connector 34. In one embodiment, another opening is formed on the end cover 36 to allow passage of a functional element, such as an optical fiber cable 5.

Figure 7:
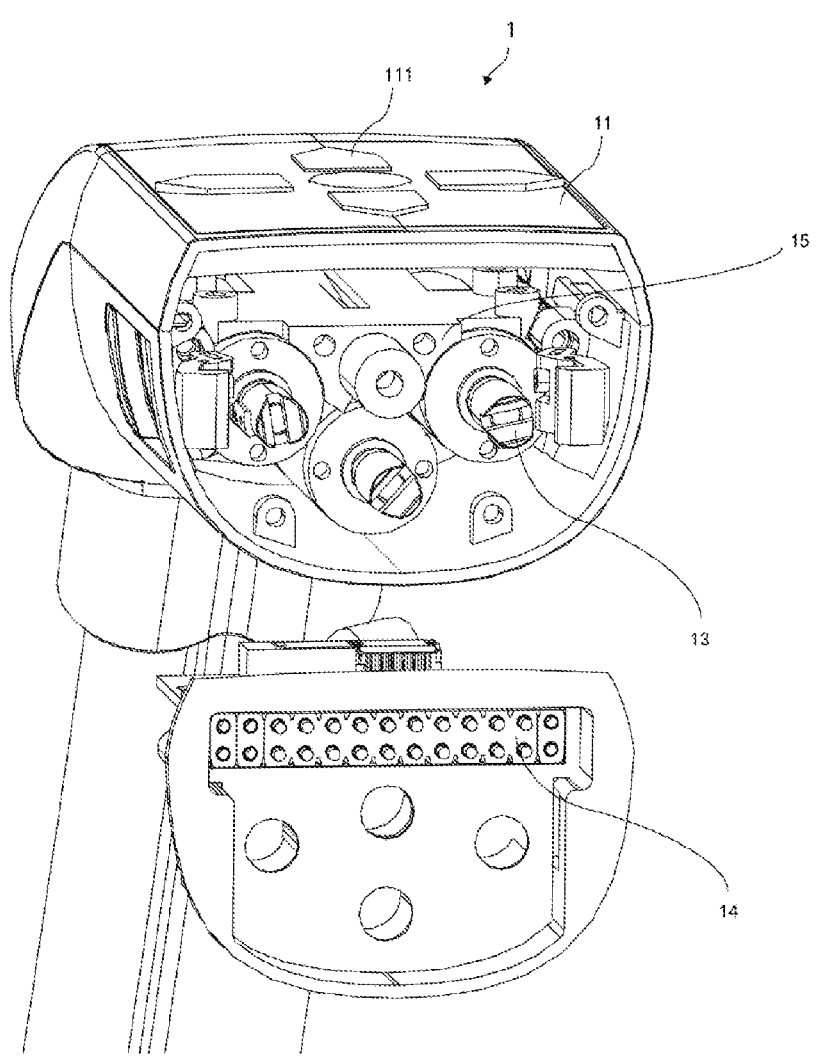
FIG. 7 shows a control handle of the endoscope system according to one embodiment of the invention.

FIG. 7 shows a control handle 1 having the second docking key 13. The control handle 1 includes a circuit board 14 in a housing 11. Preferably, the circuit board 14 on the control handle side and the electrical connector 34 on the connecting interface side are connected by a pogo pin connector. The pogo pin connector includes pogo pins disposed on the circuit board 14 and metal contacts disposed on the electrical connector 34. Preferably, the pogo pins are arranged on the control handle side, and the metal contacts are arranged on the connecting interface side. As such, the pogo pins do not require sterilization and the risk of damaging the pogo pins is reduced.

Figure 8:
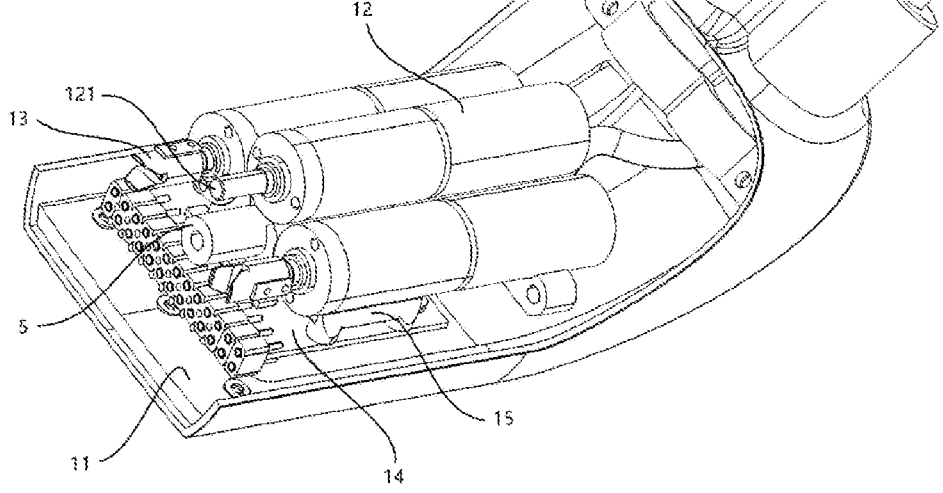
FIG. 8 is an enlarged view of showing components in the control handle in FIG. 7.

As illustrated in FIG. 8, the control handle 1 comprises at least one electric motor 12. The second docking key 13 is mounted to an output end of the motor 12, for example, to the output shaft 121 of the motor 12. A bracket 15 is arranged in the housing 11 of the control handle 1 to support the motor 12. In one embodiment, three motors 12 are located in the control handle 1 and are supported by the bracket 15. It is understood that any number of motors could be used and the number of motor may correspond to the number of capstan assembly in the connecting interface 3.

Figure 9:
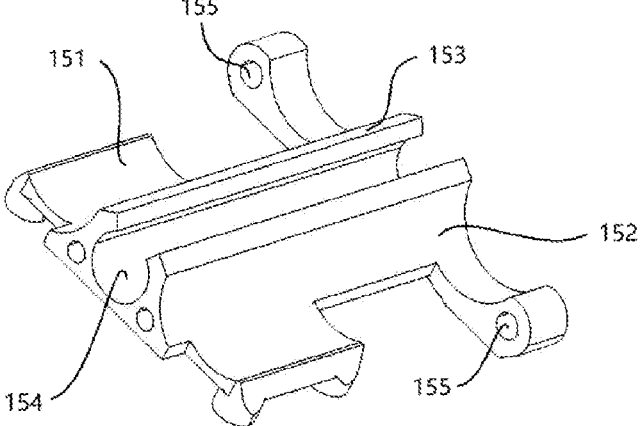
FIG. 9 shows the bracket in the control handle.

FIG. 9 shows the structure of the bracket 15. Two curved surfaces 151, 152 are provided on two sides of the bracket 15 for holding two cylindrical motors. The two curved surfaces 151, 152 are separated by a tubular structure 153 which defines a slot 154 or a tube. The upper surface of the tubular structure 153 can support another motor. The slot 154 or tube is used to receive a functional element such as an optical fiber cable 5. Further, the circuit board 14 can be arranged between the bracket 15 and the housing 11 of the control handle 1. The bracket 15 provides support to various components in the control handle 1. Accordingly, the space of the control handle is fully utilized.

Back to FIG. 7, control elements 111 are provided on the control handle 1 to allow a user to control the movement of the flexible tip 2A and/or the image sensor module 21. At least one control element 111 is designed to actuate more than one motor, at the same time or following a particular sequence, to control the flexible tip 2A to perform a complex movement or to exhibit a complex shape.

The control element 111 can be in the form of a button, a joystick, a touch screen, or the like. The control logic can be preset for different control elements 111, or can be programmed by user. For example, one button can be set to change the shape of the flexible tip 2A from a straight line to an S-shaped curve so that a bird-eye view of a surgical site can be obtained by the image sensor module. It is also possible to record the user's control of different motors in a period of time and save it in a memory. The recorded control can be triggered by a control element 111 so that the user can easily repeat the desired control. This enables the user to quickly change the flexible tip 2A to multiple desired shapes with a minimum operation of the control elements 111. Accordingly, reliability and efficiency of the control of the endoscope system are significantly improved.

Figure 10:
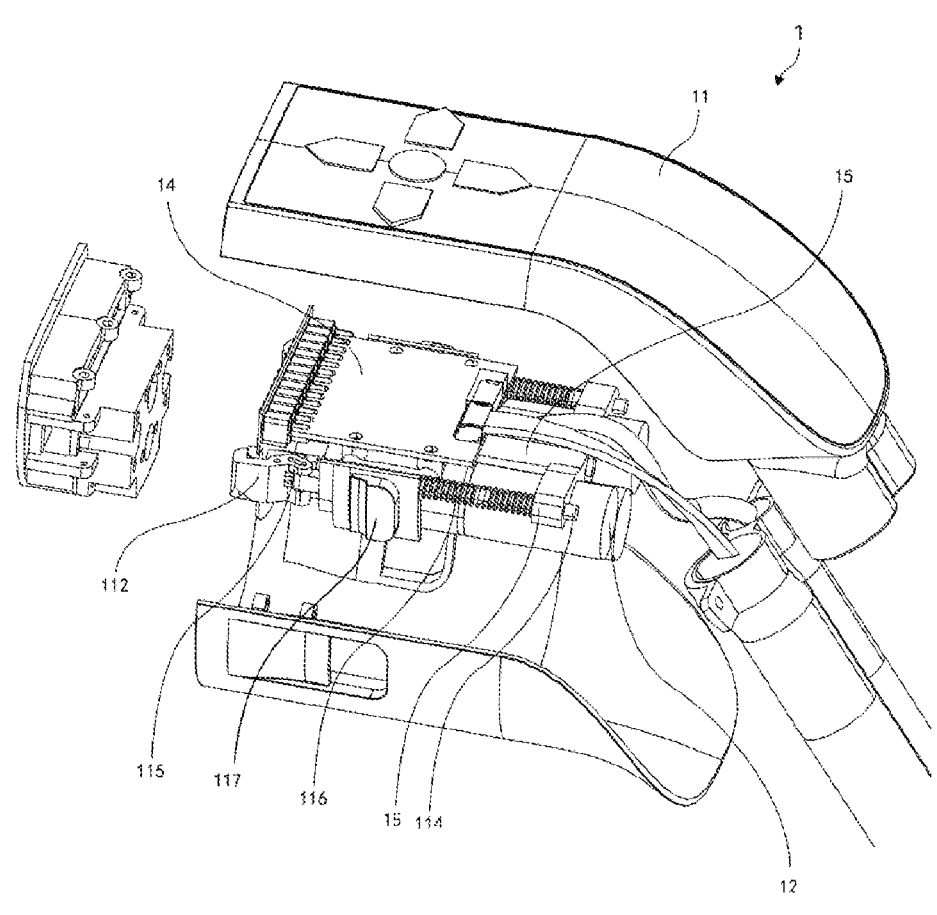
FIG. 10 is an exploded view of the control handle.
Figure 11:
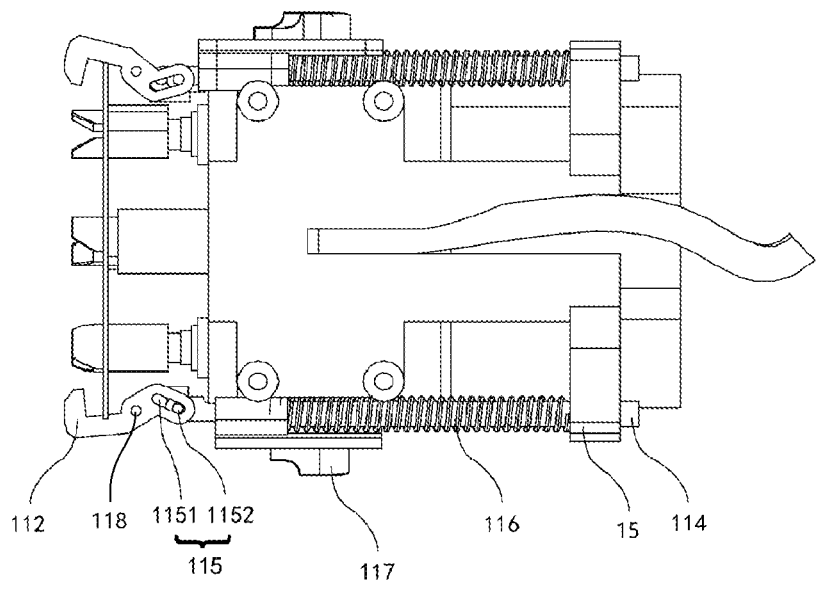
FIG. 11 shows the locking means on the control handle.

To ensure that the movement of the second docking key 13 can be transmitted stably and uninterruptedly to the drive tendon 4 during the use of the endoscope system, a locking means is provided on the control handle 1. As illustrated in FIGS. 10 and 11, the locking means includes a latch 112 and an operating member 117. The operating member 117 is movable to engage the latch 112 with or disengage the latch 112 from a catch slot 35 (shown in FIG. 2) formed on the end cover 36 of the connecting interface 3.

The locking means further includes a rod 114 and a spring 116. The rod 114 extends longitudinally in the control handle 1. In one embodiment, the rod 114 passes through the openings 155 (shown in FIG. 9) formed on the bracket 15. The operating member 117 is designed to be slidable along the rod 116. For example, the operating member 117 is formed with a hole into which the rod 116 extends. The operating member 117 is biased by the spring 116 to a locked position when no external force is applied to the operating member 117.

The latch 112 is coupled to the operating member 117 so that the sliding movement of the operating member 117 causes the latch 112 to engage with or disengage from the catch slot 35. In one embodiment, the latch 112 is coupled to the operating member via a linkage mechanism 115. As best seen in FIG. 11, the linkage mechanism 115 includes an elongated slot 1151 at one end of the latch 112 and a bar 1152 on the operating member 117. The linkage mechanism 115 converts a linear motion of the operating member 117 into a rotational motion of the latch 112 around a pivot 118.

To release the lock between the connecting interface 3 and the control handle 1, a user slides the operating member 117 against the biasing force of the spring 116. At the same time the bar 1152 starts to move in the elongated slot 1151. Since the elongated slot 1151 is oriented at an angle relative to the longitudinal direction, linear movement of the bar 1152 causes the latch 112 to rotate around the pivot 118 in the counter-clockwise direction. FIG. 11 shows the state where the bar 1152 has reached the end of the elongated slot 1151 and the latch 112 has been rotated to an unlocking position.

Figure 12:
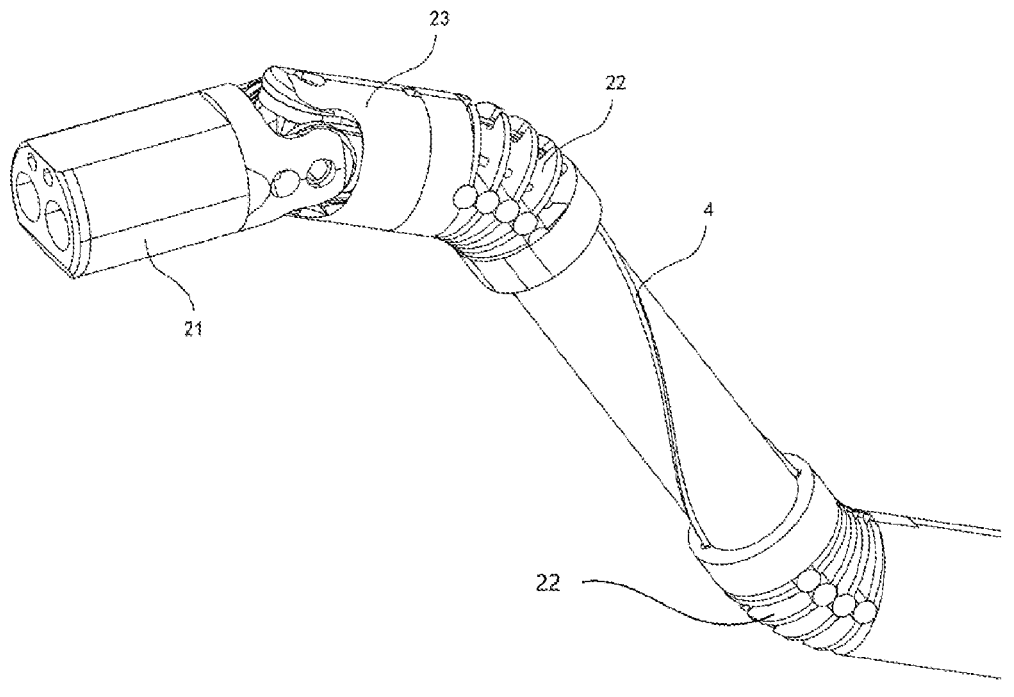
FIG. 12 shows the flexible tip and image sensor module according to one embodiment of the invention.
Figure 13:
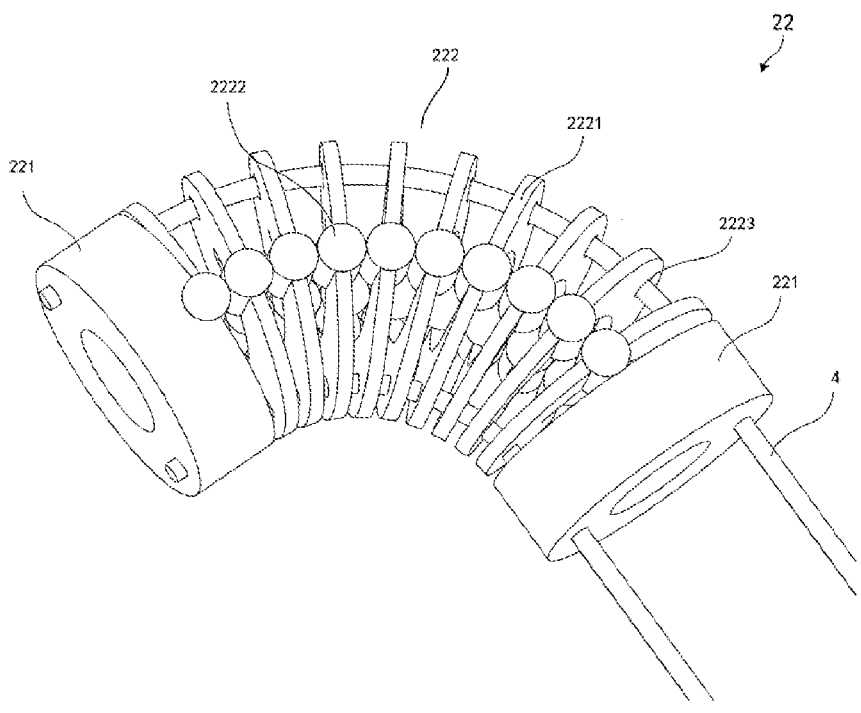
FIG. 13 shows the flexible joint in FIG. 12.

FIG. 12 shows the flexible tip 2A of the endoscope system. The image sensor module 21 is connected to the flexible tip 2A by means of a gimbal joint 23. In this embodiment, the flexible tip 2A has two flexible joints 22. It should be noted that any number of flexible joint can be used. FIG. 13 shows one flexible joint 22 comprising two support sections 221 and an articulating section 222 connected between the two support sections 221. The articulating section 222 includes a plurality of segments 2221 each provided with at least one contact assisting part 2222. In one embodiment, a pair of contact assisting part 2222 is arranged at diametrically opposite positions on each segment 2221. When the flexible joint 22 bends under the action of the drive tendons 4, the contact assisting part 2222 of the adjacent segments 2221 are in contact with each other. At least one tendon hole or slot 2223, through which a drive tendon 4 passes, is formed on each segment 2221 of the articulating section 222. Preferably, the contact assisting part 2222 has a circular or elliptical cross section.

In one embodiment, a plurality of segments 2221 is connected with each other in a helical manner to form a spring-like structure. A helical articulating section 222 makes it possible to distribute the torsional force and bending force uniformly on each segment 2221, thereby achieving a better flexibility. Alternatively, the segments 2221 can be in the form of concentric rings or discs.

Provision of the contact assisting parts 2222 helps to control the bending angle of the flexible joint and also prevents misalignment between adjacent segments. Preferably, the segments 2221 can be made of a soft material to reduce the tension required to actuate the flexible joint 22.

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, the terminology "present invention" or "invention" may be used as a reference to one or more aspect within the present disclosure. The language present invention or invention should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features.

The invention claimed is:

1. A flexible endoscope system, comprising:
   (i) a head part, comprising:
      a shaft (2);
      a first drive tendon (4) extending in the shaft (2);
      a flexible tip (2A) located at a distal end of the shaft (2), movement of the flexible tip being controlled by the first drive tendon (4);
      a connecting interface (3) located at a proximal end of the shaft (2), the connecting interface including a first capstan assembly (31) around which the first drive tendon (4) is wound; and
      an image sensor module (21) arranged on the flexible tip (2A); and
   (ii) a control handle (1) detachably connected to the connecting interface (3), wherein the control handle (1) includes at least one motor (12), a bracket (15) for supporting the at least one motor (12), and a circuit board (14) arranged between the bracket (15) and a housing (11) of the control handle (1);
   wherein the first capstan assembly (31) includes a capstan shaft (311) having a first docking key (32), and the control handle includes a second docking key (13) coupled to an output end of the motor (12), when the control handle (1) is coupled to the connecting interface (3), the second docking key (13) mates with the first docking key (32) such that movement of the second docking key can be transmitted to the first capstan assembly via the first docking key to adjust the tension in the first drive tendon (4).

2. The flexible endoscope system according to claim 1, wherein one of the first and second docking keys (32, 13) has a projecting portion (321), and the other of the first and second docking keys (32, 13) has a recessed portion (131) complementary in shape, at least one of the first and second docking keys (32, 13) is provided with a guiding portion (322, 132) to facilitate the engagement between the first and second docking keys (32, 13).

3. The flexible endoscope system according to claim 1, wherein the connecting interface (3) includes a tendon guide (331) near a proximal end of the shaft (2), at least a portion of an inner wall of the tendon guide (331) is provided with a guide groove (332) for receiving and guiding a segment of the first drive tendon (4) between the proximal end of the shaft (2) and the first capstan assembly (31).

4. The flexible endoscope system according to claim 3, wherein the connecting interface (3) further includes a base (33) located between the proximal end of the shaft (2) and the tendon guide (331), a hole (330) is formed on the base (33) for receiving one end of the capstan shaft (311), a bearing (333) is arranged in the hole (330) for rotatably supporting the capstan shaft (311).

5. The flexible endoscope system according to claim 1, wherein a second drive tendon (4) is wound on the first capstan assembly (31), the first capstan assembly (31) includes two positioning rings (312) along the capstan shaft (311), each of the positioning rings (312) has an axially extending portion (3122) on which one drive tendon (4) is wound and a stopper (313) for holding an end of the respective drive tendon (4).

6. The flexible endoscope system according to claim 5, a fastening hole (3121) is provided on each of the positioning rings (312) for receiving a fastener used to lock the positioning rings (312) on the capstan shaft (311).

7. The flexible endoscope system according to claim 1, wherein the connecting interface (3) further includes an end cover (36) on which openings are formed for receiving an electrical connector (34) and an optical fiber connector (5).

8. The flexible endoscope system according to claim 7, wherein the circuit board (14) is connected to the electric connector (34) by means of a pogo pin connector.

9. The flexible endoscope system according to claim 1, wherein a locking means is provided on the control handle (1), the locking means includes a latch (112) and an operating member (117) movable by a user to engage the latch (112) with or disengage the latch from a catch slot (35) formed on the connecting interface (3).

10. The flexible endoscope system according to claim 9, wherein the locking means further includes a rod (114) along which the operating member (117) is slidable and an elastic element (116) for biasing the operating member (117) to a locking position, the latch (112) is coupled to the operating member (117) via a linkage mechanism (115) which converts a sliding movement of the operating member (117) into a rotational motion of the latch (112).

11. The flexible endoscope system according to claim 10, wherein the linkage mechanism (115) includes an elongated slot (1151) on the latch (112) and a bar (1152) on the operating member (117), the elongated slot (1151) is oriented at an angle relative to a longitudinal direction such that movement of the bar (1152) in the elongated slot (1151) causes the latch (112) to rotate.

12. The flexible endoscope system according to claim 1, wherein the bracket (15) has two curved surfaces (151, 152) for supporting two motors (12), the two curved surfaces (151, 152) are separated by a tubular structure (153) which defines a slot (154) or a tube for receiving an optical fiber cable (5).

13. The flexible endoscope system according to claim 1, wherein the head part is disposable and the control handle is durable.

14. The flexible endoscope system according to claim 1, wherein the flexible tip (2A) includes at least one flexible joint (22), each flexible joint comprises two support sections (221) and an articulating section (222) connected therebetween, the articulating section (222) includes a plurality of segments (2221) each provided with at least one contact assisting part (2222), wherein the contact assisting parts (2222) of adjacent segments (2221) are in contact with each other when the flexible joint (22) bends.

15. The flexible endoscope system according to claim 14, wherein a pair of contact assisting parts (2222) is arranged at diametrically opposite positions on each segment (2221), and at least one tendon hole or slot (2223) is formed on each segment (2221).

16. A flexible endoscope system, comprising:
(i) a head part, comprising:
   a shaft (2);
   a plurality of drive tendons (4) extending in the shaft (2);
   a flexible tip (2A) located at a distal end of the shaft (2),
   a connecting interface (3) located at a proximal end of the shaft (2), the connecting interface including first, second and third capstan assemblies (31), a pair of drive tendons (4) being wound around each of the first, second, and third capstan assemblies (31), respectively, to control the movement of the flexible tip (2A) in one degree of freedom; and
   an image sensor module (21) arranged on the flexible tip (2A); and
(ii) a control handle (1) detachably connected to the connecting interface (3), wherein the control handle (1) includes first, second, and third motors (12) for independently actuating the first, second, and third capstan assemblies (31), respectively,
wherein the first capstan assembly (31) includes a capstan shaft (311) having a first docking key (32), and the control handle includes a second docking key (13) coupled to an output end of the first motor (12), when the control handle (1) is coupled to the connecting interface (3), the second docking key (13) mates with the first docking key (32) such that movement of the second docking key can be transmitted to the first capstan assembly via the first docking key to adjust the tension in the pair of drive tendons (4) associated with the first capstan assembly (31), and
wherein one or more control elements (111) are provided on the control handle (1), at least one control element (111) being preset or programmed to control one or more of the first, second and third motors (12) to trigger a movement of the flexible tip (2A) and/or the image sensor module (21).

17. The flexible endoscope system according to claim 16, wherein the one or more control elements (111) is preset or programmed to cause the flexible tip (2A) to exhibit an S shape so that a bird-eye view of a surgical site can be obtained by the image sensor module (21).

* * * * *